United States Patent
Daskalon et al.

(10) Patent No.: US 6,613,273 B2
(45) Date of Patent: Sep. 2, 2003

(54) METHOD FOR THE MANUFACTURE OF DENTAL RESTORATIONS

(75) Inventors: Gregg Daskalon, Orange, CT (US); Arun Prasad, Cheshire, CT (US); Denise L. North, Manchester, CT (US); Elie Zammarieh, Wallingford, CT (US)

(73) Assignee: Jeneric/Pentron Incorporated, Wallingford, CT (US)

(*) Notice: Subject to any disclaimer, the term of this patent is extended or adjusted under 35 U.S.C. 154(b) by 0 days.

(21) Appl. No.: 09/757,916

(22) Filed: Jan. 10, 2001

(65) Prior Publication Data

US 2002/0009380 A1 Jan. 24, 2002

Related U.S. Application Data

(60) Provisional application No. 60/175,361, filed on Jan. 10, 2000, provisional application No. 60/182,388, filed on Feb. 14, 2000, provisional application No. 60/182,155, filed on Feb. 14, 2000, provisional application No. 60/193,591, filed on Mar. 30, 2000, and provisional application No. 60/201,067, filed on May 1, 2000.

(51) Int. Cl.[7] ............... B22F 7/04; B32B 7/02
(52) U.S. Cl. ............... 419/5; 419/9; 264/19; 433/206; 433/207; 433/208; 433/209
(58) Field of Search ............... 419/5, 9; 264/19; 433/206, 207, 208, 209

(56) References Cited

U.S. PATENT DOCUMENTS

| | | | |
|---|---|---|---|
| 3,502,466 A | | 3/1970 | Vickery |
| 4,369,068 A | | 1/1983 | Hausselt |
| 4,434,211 A | * | 2/1984 | Shoher et al. ............... 428/552 |
| 4,689,197 A | | 8/1987 | Groll |
| 4,828,495 A | | 5/1989 | Bell |
| RE33,371 E | | 10/1990 | Shoher |
| 4,980,124 A | | 12/1990 | Dimmer |
| RE35,367 E | | 10/1996 | Shoher et al. |
| 5,730,600 A | * | 3/1998 | Shoher et al. ............... 433/223 |
| 6,213,776 B1 | * | 4/2001 | Shoher et al. ............... 433/207 |
| 6,325,839 B1 | * | 12/2001 | Prasad et al. ............... 75/247 |

FOREIGN PATENT DOCUMENTS

EP  0 523 019 A2  1/1993

OTHER PUBLICATIONS

International Search Report dated Mar. 22, 2002.
Sinterkor Instruction Manual, Jul., 2000, Rev. 3.1, Published by: Jeneric/Pentron, Inc., Wallingford, Connecticut 06492 U.S.A. 40 Pages.
Jeneric/Pentron, Inc., SinterKor Instruction Manual, Rev 3.1, Jul., 2000.
Nobil Metal, Sintercast Gold Instruction Manual in Italian–with Certified Translation from English Translation.

* cited by examiner

*Primary Examiner*—Daniel J. Jenkins
(74) *Attorney, Agent, or Firm*—Ann M. Knab

(57) ABSTRACT

Dental restorations are fabricated using metal powder. Preferably, the metal powder is a high fusing metal and preferably, the metal powder comprises a non-oxidizing metal. The metal powder is applied to a die and is covered with a covering material such as a refractory die material preferably in the form of a flowable paste. A second covering material may be sprinkled or dusted onto the paste. The model is then dried prior to firing. After drying, the model is sintered to provide a high strength metal restoration. After sintering, the outer shell can be broken off easily with one's hand to expose the sintered coping.

158 Claims, 7 Drawing Sheets

METHOD FOR THE MANUFACTURE OF DENTAL RESTORATIONS

CROSS-REFERENCE TO RELATED APPLICATIONS

This is application claims priority to U.S. Provisional Application Nos. 60/175,361 filed Jan. 10, 2000, 60/182,388 filed Feb. 14, 2000, 60/182,155 filed Feb. 14, 2000, 60/193,591 filed Mar. 30, 2000 and 60/201,067 filed May 1, 2000, all of which are incorporated herein by reference.

FIELD OF THE INVENTION

The present invention relates generally to a method of manufacturing dental restorations and restorations produced therefrom and more specifically a method of using metal powders to manufacture dental restorations.

BACKGROUND OF THE INVENTION

Conventional techniques used in the manufacture of dental restorations involve the casting of materials such as metals and ceramics and employ the "lost wax" process. As known in the industry, the lost wax technique consists of a number of successive operations which begin with the dentist taking an impression of the patient's teeth. The impression allows a model or die to be made of the teeth, which the dental technician then uses to build a wax pattern thereon of the article to be made. The wax is burned out and the metal, alloy or ceramic is cast into the void left by the wax. This process is time consuming and involves complex steps.

Alternative methods have been proposed including those involving the sintering of metals. In many of the methods, more than one heating step is required to obtain the metal core. In U.S. Pat. No. Re. 33,371, metal powder is applied to a model and heated. A second application of metal powder is performed and the model is heated again. In addition to the many required heating steps, the metallic mixture may run on the model before sintering, thus damaging the dimensional accuracy of the product and making it difficult to achieve consistent thickness.

In EP 523019, metal powder is applied onto a model and the model must then be plunged into a small paper cylinder, filled with a material, known as covering material. The material prevents running and deformation and is mechanically removed when sintering has been performed. Although the covering material filled in the cylinder is able to prevent the material from running, the inventors herein have found that the covering material used in the cylinder is too thick and promotes tearing and cracking on the metal coping.

It is desirable that metal restorations be provided having no cracking and tearing problems. It is beneficial that the manufacturing steps be reduced to provide high strength dental restorations.

SUMMARY OF THE INVENTION

These and other objects and advantages are accomplished by the process wherein metal powder materials are used to form dental restorations. In one embodiment herein, metal powder is applied to a die or model of a tooth for which a restoration will be made. The metal powder may comprise one or more precious metals, non-precious metals and alloys thereof. Preferably, the metal powder is a high fusing metal and preferably, the metal powder comprises a non-oxidizing metal. The metal powder may comprise a multimodal particle size distribution to achieve high density during sintering. The multimodal particle powder comprises larger or coarse particle size powder in combination with a smaller or fine particle size powder. After the metal powder is applied to the model, it is covered with a covering material such as a refractory die material preferably in the form of a flowable paste. Optionally, after the flowable paste has been applied onto the metal powder, a second covering material may be sprinkled or dusted onto the paste. The model is then dried prior to firing. After drying, the model is sintered to provide a high strength metal restoration. The sintering range depends upon the metal or alloy being used. The sintering temperature is close to but below or in the low range of the melting temperature range of the layer of alloy powder, or if a metal powder is used, the sintering temperature will be close to, but below the melting point of the metal powder. After sintering, the outer shell can be broken off easily with one's hand to expose the sintered coping. The coping is then easily removed from the die absent any adherence problems.

In an alternate embodiment of the process herein, after a high melting metal powder has been applied to the die, a mass or ball of lower melting metal or alloy or powder of metal or alloy is placed or disposed on the metal powder layer. The mass acts as a reservoir of material which will flow into the metal powder interstices formed from the first metal or alloy layer. The process continues as above, whereafter sintering, the outer shell can be broken off easily with one's hand to expose the sintered coping. The coping is then easily removed from the die absent any adherence problems.

In yet another embodiment herein, after the metal powder layer is applied to the die, a ceramic or porcelain material is applied to the unsintered metal layer. The porcelain appears to act as a thermal barrier to help in holding the coping in place, prevent margin creeping and lifting. There is no need to apply a covering layer prior to sintering and there is no need to apply an opaque layer after the sintering process and prior to finishing the coping with porcelain to achieve the finally desired product.

The invention also includes various finishing processes including pressing ceramic onto the metal coping or applying fiber-reinforced composite materials or polymeric materials to the metal copings.

The processes and materials herein may be used to manufacture dental appliances including but not limited to orthodontic retainers, bridges, space maintainers, tooth replacement appliances, dentures, posts, crowns, posts, jackets, inlays, onlays, facings, veneers, facets, implants, abutments, splints, partial crowns, teeth, cylinders, pins, and connectors.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

Figure 1:
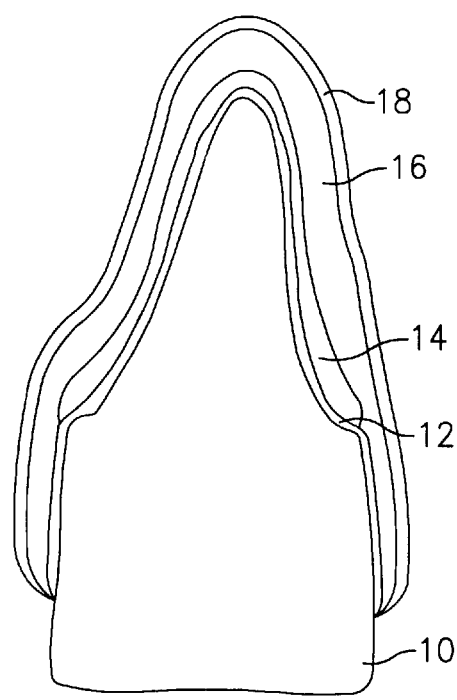
FIG. 1 is a cross-sectional view of a die with materials thereon in the manufacture of a dental restoration in accordance with a process herein.

As will be appreciated, the present invention provides a method of manufacturing dental restorations using metal powder materials to form the restorations. In one embodiment of the process, a model or duplicate model of a tooth to be restored is fabricated. This involves known techniques whereby a dentist takes an impression of the tooth or teeth to be restored. A master die is then prepared from the impression using a suitable die material. A duplicate working or refractory die or model is made from the original impression or from a duplicate impression prepared from the master die.

Metal powder is then applied to the die or model of the tooth for which a restoration will be made. Prior to application of metal powder, the die may be coated with a thin layer of die sealer/spacer material or similar material such as SinterKor™ Die Spacer available from Jeneric/Pentron Inc., Wallingford, Conn., to seal the die and to provide easy removal of the restoration from the die at the completion of the sintering operation. Die seal/spacer materials should preferably leave no residue after burning.

The metal powder may be mixed with a binder material to hold the metal particles together for easier application or adaptation to the die. The combination metal powder/binder is preferably in a paste, tape or sheet form. Commercially available SinterKor™ materials may be used herein, available from Jeneric/Pentron Inc., Wallingford, Conn., and also as disclosed in the SinterKor™ Instruction Manual from Jeneric/Pentron, Revision 3.1, 7/2000, which is hereby incorporated by reference for all materials and processes herein. Accordingly, the paste may be pressed onto and around the die or the sheet may be cut to a desired shape to fit onto the die. In most instances, it is important that the applied layer extend fully to the margins.

The thickness of the metal layer is dependent upon the restoration being fabricated. For example, in making abutments, the thickness of the metal layer may range from about 0.1 to about 0.5 mm, and preferably from about 0.1 to about 0.3 mm. In making pontics, the thickness of the metal layer may be greater, and can be accomplished either by folding thin layers or forming into a thick mass.

Typical binder materials include, but are not limited to filler-free wax, ammonium caseinate, ammonium stearate, pectin, hexamine, ethyl cellulose, anthracene, triacetyl starch, dulcin, carbazole and tetraphenyl ethylene. The binder may be mixed with a solvent prior to mixing with the metal powder. Solvents include, without limitation, propylene glycol, water, eugenol, light paraffin oil, butyl acetate, butyl benzoate, diacetone alcohol, and dibutyl phthalate. The binder and solvent are driven off during the sintering process.

The powder/binder mixture comprises from about 90 to about 99 percent powder and from about 1 to about 10 percent binder. Preferably, the powder is present in about 95% by weight and the binder is present in about 5% by weight.

The metal powder may comprise one or more precious metals, non-precious metals and alloys thereof. Preferably, the metal powder is a high fusing metal and preferably, the metal powder comprises a non-oxidizing metal. More preferably, the metal powder is selected from one or more of gold, platinum, silver and alloys thereof whereby the alloys may comprise one or more of the metals in combination with one another or with a different metal, such as copper, rhodium, palladium, indium, tin, gallium and mixtures thereof. One preferred alloy comprises about 85 to about 99% Au, 0 to about 15% Pt, and 0 to about 15% of one or more of Ag, Pd, Rh, In, Rn, and Ta.

The metal powder may comprise a multimodal particle size distribution to achieve high density during sintering. The multimodal particle powder comprises larger or coarse particle size powder in combination with a smaller or fine particle size powder. The average size of the coarse particle powder is about 25 microns, with the majority of the particles exhibiting diameters in the range from about 5 to about 100 microns and preferably with the maximum size no greater than about 44 microns (−325 mesh) to about 50 microns (−270 mesh). The fine particle size is less than about 5 microns and preferably less than about 2 microns. The coarse particles are present in an amount in the range of about 85 to about 95% by weight and the fine particles are present in an amount in the range of about 5 to about 15% by weight of the powder.

After the metal powder has been applied to the die, it may be soaked in a solvent such as alcohol or acetone. After the metal powder is applied to the model, with or without the step of soaking in acetone, it is covered with a covering material such as a refractory die material. Typical refractory die materials are compatible with all types of dental alloys used in dentistry. These materials may be in the form of flowable suspensions or pastes and comprise a powder in combination with a liquid vehicle such as alcohol, acetone and the like. It is important that the die material is applied at a certain thickness so as to prevent cracking and tearing of the metal restoration during sintering. It was found that if too thick of a layer is used, cracking and tearing occur on the metal restoration. These materials may be in dry powder form (dry technique) or in the form of flowable suspensions or pastes that comprise a powder in combination with a liquid vehicle (wet technique). When using the wet technique, the refractory layer is preferably in the range from about 1 to about 8 mm, and more preferably, equal to or below about 5 mm in thickness and most preferably, equal to about 4 mm in thickness. When the dry technique is used, it is recommended that a container such as a quartz tube be placed around the model with the metal thereon to contain the dry powder which surrounds the model. The thickness of the layer when using the dry technique is approximately the same as that when using the wet technique. Investment refractory materials useful herein include gypsum-bonded, phosphate-bonded or ethyl silicate-bonded investment materials. These investment materials normally contain up to 80% of a refractory filler such as quartz, cristobolite, other forms of silica, leucite or mixtures thereof. These investment materials are commercially available and are widely used in dental laboratories for various purposes. Examples of commercially available investment materials include Rapid-Vest® investment available from Jeneric®/Pentron® Inc., Wallingford, Conn.; Accu-Press™ investment available from Talladium Inc., Valencia, Calif.; PC15™ investment available from WhipMix Corporation, Louisville, Ky.; and Speed™ investment available from Ivoclar North America, Amherst, N.Y.

Optionally, after the flowable paste has been applied onto the metal powder, a second covering material may be sprinkled or dusted onto the wet paste. The second covering material is preferably a high temperature refractory powder. It is preferable that the high temperature refractory powder is applied directly after the paste has been applied to prevent slumping and movement of the paste. The high temperature refractory powder improves the green strength of the paste material. The externally applied material insulates the metal powder layer from furnace overshoot during sintering. It is also beneficial in breaking and removing the shell from the restoration after the sintering process. The removal process is facilitated by the rough texture created by the high temperature refractory powder. Examples of the high temperature refractory powder include but are not limited to high temperature refractory oxides such as alumina, silica, and the like. Preferably, the high temperature refractory powder has a melting temperature equal to or greater than about 1200° C.

The model is then dried prior to firing. After drying, the model is sintered to provide a high strength metal restoration. The sintering range depends upon the metal or alloy being used. The sintering temperature is close to but below or in the low range of the melting temperature range of the layer of alloy powder, or if a metal powder is used, the sintering temperature will be close to, but below the melting point of the metal powder. After sintering, the outer shell can be broken off easily with one's hand to expose the sintered coping. The coping is then easily removed from the die absent any adherence problems.

Figure 2:
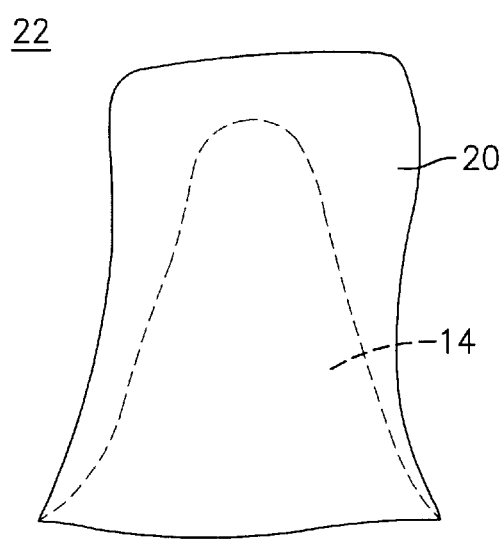
FIG. 2 is the finished restoration of the coping shown in FIG. 1.

FIG. 1 illustrates one example of the invention. Die 10 is shown having die spacer material 12 applied thereto. Metal powder in the form of a tape 14 is applied to die 10 over die spacer 12. A layer of refractory die material 16 is then applied over metal powder layer 10. High temperature refractory powder 18 is shown applied over the refractory die material. The material is then sintered to provide a high strength dental core material. The outer covering layers are removed from what is now core 14 which is further removed from die 10 as shown in FIG. 2. Thereafter, an opaque layer or porcelain or composite is applied to core 14 to block out the metal followed by a porcelain or composite layers 20, such as commercially available Snyspar® porcelain or commercially available Sculpture® composite, both available from Jeneric/Pentron Inc., Wallingford, Conn. followed by firing or curing procedures to form the final dental restoration 22.

In an alternate embodiment of the process herein, after a high melting metal powder has been applied to the die, a mass or ball of lower melting metal or alloy or powder of metal or alloy is placed or disposed on the metal powder layer. The mass of metal may be bonded, glued, melted or mechanically adhered to the metal powder on the model. The bonding material will have a low melting temperature such that it will burn out at low temperatures. The mass of metal or alloy may be in the form of a solid piece of metal, or an ingot or may be an agglomerate or mass of metal or alloy powder held together by a binder. The mass is preferably in the shape or form of a ball, sphere, bar, oval, block, or similar shape. The mass acts as a reservoir of material which will flow into the metal powder interstices formed from the first metal or alloy layer. If a solid metal form is used, it should be coated with a wax or die spacer material in order to counteract expansion stresses. Preferably, the mass or reservoir is placed on or proximate the top of the die or model and will flow over and down around the high fusing metal powder on the model during heat treatment and into the interstices of the high fusing metal structure, although placement of the reservoir may be any suitable position to allow the reservoir to flow into the metal or alloy core layer. Powders having larger particle sizes compared to the particle size of the metal layer are preferred to make the metal reservoir, such as, as high as 250 microns. The mass of the second metal, alloy or powder thereof is approximately equal to the weight of the first metal or alloy powder layer.

The reservoir or mass of metal or alloy may include any low fusing metal or alloy such as gold, gold alloys, or similar low-fusing alloys. The alloys may contain small amounts of oxidizable elements such as Ga, Zn, Ge, Ag, Pd, Rh, In, Ru, Cu, Sn, Ta and other precious metals. If an oxidizing element is used in either the metal layer or the mass, provisions can be made to generate a reducing or inert atmosphere to prevent oxidation during the sintering operation. Reducing or inert atmosphere may be created in a variety of ways. Reducing gases such as formic gas or inert gas, e.g., argon, may be flowed into the sintering chamber. Alternatively, a carbonaceous material may be incorporated onto or placed over the thermal barrier layer described earlier. One example of placing a carbonaceous material over the barrier layer is the use of a graphite cover. Otherwise, carbonaceous material may be ground into and mixed with the outer covering layer to provide reducing atmosphere effects.

Prior to sintering, and after the reservoir has been applied, a die spacer or similar material such as SinterKor™ Die Spacer available from Jeneric/Pentron Inc., Wallingford, Conn., may be applied over the metal powder layer and reservoir. After the metal powder and metal mass have been applied to the model, the model with the materials thereon is covered with a covering material, as in the process described above, such as a refractory die material such as Polyvest™ material available from Whip-Mix Corp., Kentucky. Prior to covering with refractory die material, the die may be soaked in a solvent such as alcohol or acetone. Typical refractory die materials are compatible with all types of dental alloys used in dentistry. These materials may be in dry powder form (dry technique) or in the form of flowable suspensions or pastes that comprise a powder in combination with a liquid vehicle (wet technique). Preferably, the liquid vehicle is nonaqueous such as acetone, alcohol and the like. It is important that the die material is applied at a certain thickness so as to prevent cracking and tearing of the metal restoration during sintering. It was found that if too thick of a layer is used, cracking and tearing occur on the metal restoration. When using the wet technique, the refractory layer is preferably in the range from about 1 to about 8 mm, and more preferably, equal to or below about 5 mm in thickness and most preferably, equal to about 4 mm in thickness. When the dry technique is used, it is recommended that a container such as a quartz tube be placed around the model with the metal thereon to contain the dry powder which surrounds the model.

If the wet technique is used, the model is then dried prior to firing. After drying, the model is sintered to provide a high strength metal restoration. The sintering range depends upon the metal or alloy being used. The sintering temperature is close to but below or into the low range of the melting temperature range of the layer of alloy powder, or if a metal powder is used, the sintering temperature will be close to, but below the melting point of the metal powder. In both cases, the sintering temperature will be higher than the melting temperature range or melting point of the metal or alloy reservoir. This heat treatment allows the reservoir of metal to flow into the interstices of the layer of metal or alloy and form a dense, high strength structure. After sintering, the outer shell can be broken off easily with one's hand to expose the sintered coping. The coping is then easily removed from the die absent any adherence problems. Alternatively, if the dry technique is used, the outer covering layer is easily removed by pushing it through the quartz tube.

Figure 3:
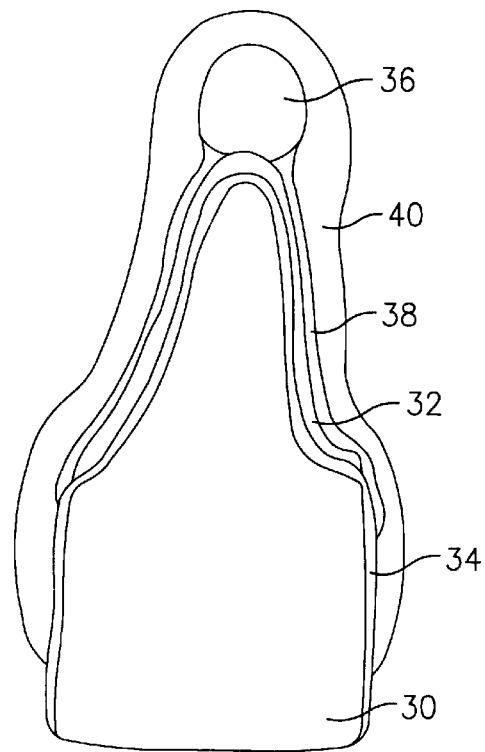
FIG. 3 is a cross-sectional view of a die with materials thereon in the manufacture of a dental restoration in accordance with a process herein.

Reference is made to FIG. 3 that shows a model 30 with a layer of metal powder 32 thereon. Die spacer material 34 is applied prior to the application of the layer of metal powder. Thereafter, a spherical-shaped reservoir of metal or alloy 36 is placed proximate the top of the model. Thereafter, a die spacer material 38 is applied on metal layer 32. Refractory covering layer 40 is then applied on and around the preceding layers and the model is sintered after evaporating acetone or alcohol from the surface of the metal. As in the process described above, optionally, after the refractory paste has been applied onto the metal powder, a high temperature refractory powder is sprinkled or dusted onto the paste. It is preferable that the high temperature refractory powder is applied directly after the paste has been applied to prevent slumping and movement of the paste. The high temperature refractory powder improves the green strength of the paste material. The combination of both the paste and the powder insulates the metal powder layer from furnace overshoot during sintering. It is beneficial in breaking and removing the shell from the restoration after the sintering process. The removal process is facilitated by the rough texture created by the high temperature refractory powder. Examples of the high temperature refractory powder include but are not limited to high temperature refractory oxides such as alumina, silica, and the like. Preferably, the high temperature refractory powder has a melting temperature equal to or greater than about 1200° C. After the covering layers have been removed, the coping is finished with porcelain or composite materials. To assist in bonding the finishing materials to the surface of the coping, a bonder coat of metal or alloy material is applied and fired thereto. The bonder material may contain gold powder with trace amounts of oxidizable elements, such as Cu, In, Sn, Rh, Pd, Ga and mixtures thereof. Pt or Ir may also be included in small quantities.

Figure 4:
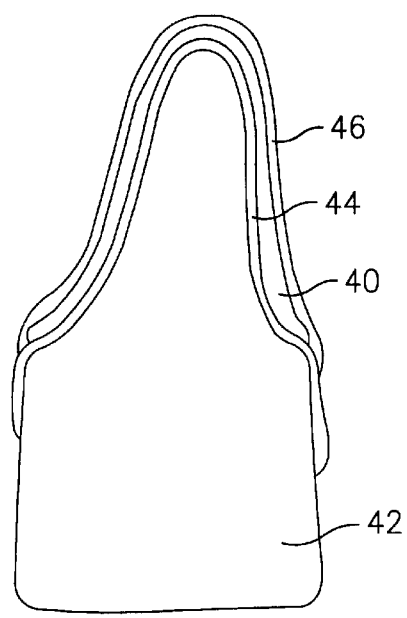
FIG. 4 is a cross-sectional view of a die with materials thereon in the manufacture of a dental restoration in accordance with a process herein.

In yet another embodiment herein, reference is made to FIG. 4, which shows metal powder layer 40 applied to die 42. A die spacer layer 44 may be applied to the die prior to application of layer 40. Thereafter, a ceramic or porcelain material 46 is applied to the unsintered metal layer. The ceramic or porcelain layer may be of a thickness necessary to cover the metal core and provide aesthetics. Preferably, the layer is in the range of about 0.1 to about 1.5 mm, and more preferably in the range of about 0.2 to about 0.5. The model with the metal and porcelain thereon is thereafter sintered. The porcelain is preferably an opaque porcelain used in the manufacture of dental restorations, such as Synspar® Opaque porcelain available from Jeneric/Pentron Inc., although any porcelain may be used herein to achieve the final result. The porcelain appears to act as a thermal barrier to help in holding the coping in place, prevent margin creeping and lifting. There is no need to apply an opaque layer after the sintering process and prior to finishing the coping with porcelain to achieve the finally desired product.

Figure 5:
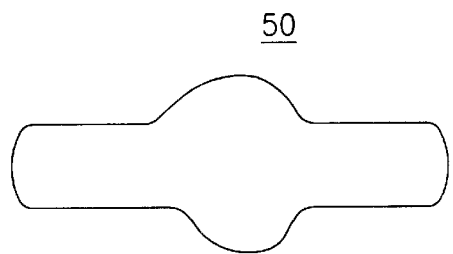
FIG. 5 is an elevational view of a pontic used in accordance with a process herein.
Figure 6:
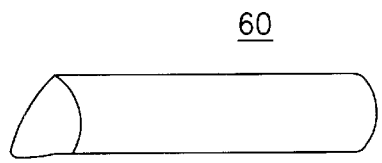
FIG. 6 is an elevational view of a bar used in accordance with a process herein.
Figure 7:
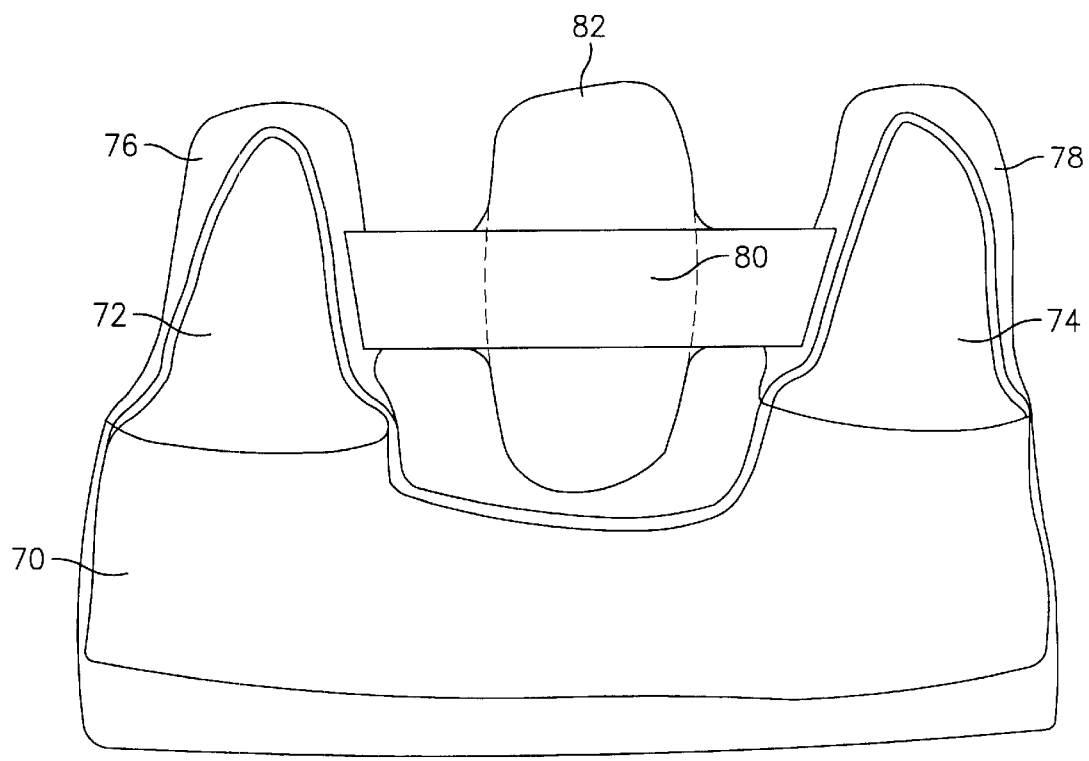
FIG. 7 is a cross-sectional view of a die with materials thereon in the manufacture of a dental restoration in accordance with a process herein.
Figure 8:
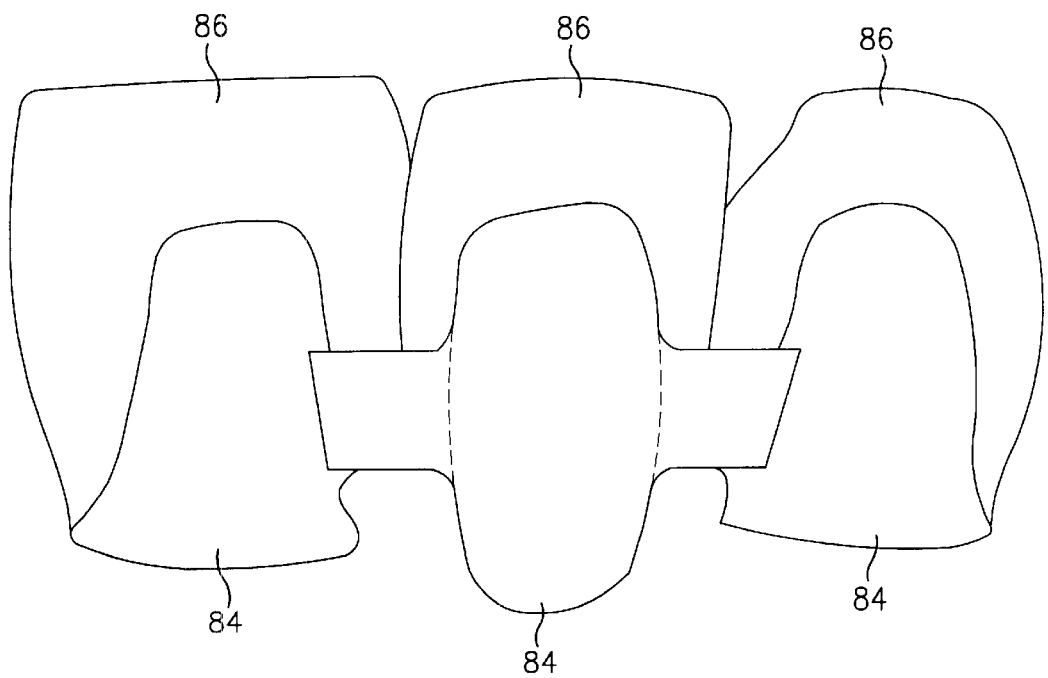
FIG. 8 is an elevational view of the finished restoration of the coping shown in FIG. 7.

The process described herein is not limited to single unit restorations, but is also applicable to multiple unit restorations. FIGS. 5 and 6 illustrate prefabricated pontic 50 and bar 60 for use in the process of the invention. Bars, pontics, blocks rods and the like may be in any shape or cross section useful in the manufacture of multiple unit restorations such as a square, rectangle, triangle, rhomboid, ovoid, and cylinder. The prefabricated components may be solid, hollow or perforated. The prefabricated component may be a solid cast metal or alloy, an extruded component, or a metal or alloy powder molded and sintered into a shaped component. Alternatively, the component may be fabricated using metal powder or sheets of metal powder and shaped at the time of fabrication. Alternately, the component may be a fiber reinforced composite material such as Sculpture/FibreKor material from Jeneric/Pentron Inc, which component may prefabricated or made when the restoration is being made. All the aforementioned processes described above for single unit restorations are also applicable to multiple unit restorations. FIG. 7 shows a die 70 having two abutment teeth sections 72 and 74. Sections 72 and 74 show metal powder 76 and 78 thereon. Bar 80 is positioned therebetween and pontic section 82 is prefabricated as part of bar 80 or, alternatively, is built onto bar 80 similarly to metal powder layers 76 and 78. Even if bar 80 is provided with a prefabricated pontic section, metal powder may further be used to build up the pontic section to the shaped desired. Thereafter, the process continues as set forth above. The entire die is covered with one or more covering layers (refractory die material and a high strength ceramic material) and sintered. The reservoir technique, as described above, may also be used in this process, whereby reservoirs of metal, alloy or powder of metals or alloys, are disposed on each section (76, 78, 82) prior to the application of the covering layer(s). After sintering, the covering layers are removed and the coping is finished with the necessary porcelain materials. FIG. 8 illustrates the final restoration with the underlying metal coping 84 and a porcelain finish layer 86.

Figure 9:
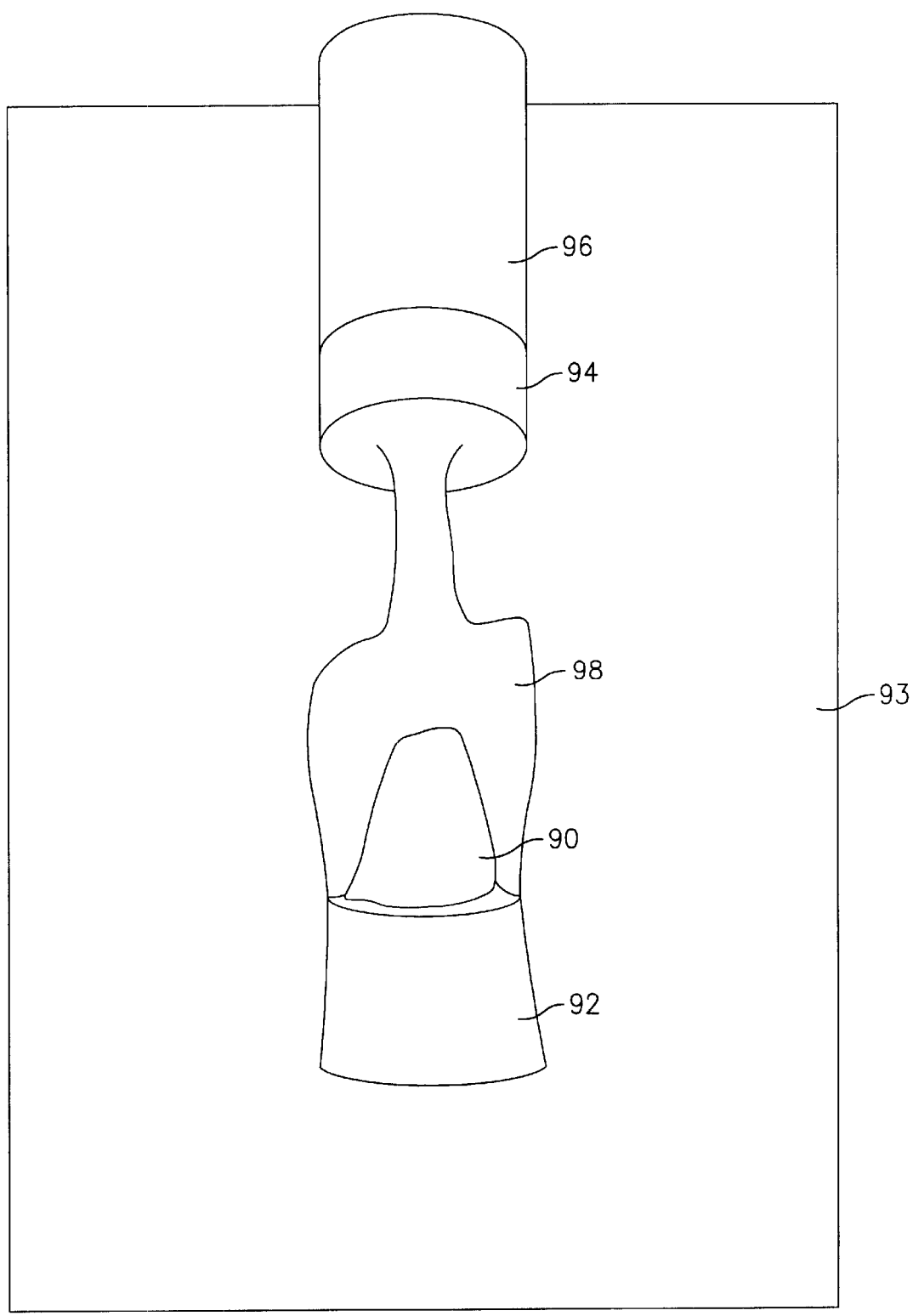
FIG. 9 shows a coping prior to having a ceramic pellet pressed thereon.

An alternative method for finishing any of the restorations (single or multiple unit) made by the processes discussed herein may involve pressing a ceramic material such as OPC® porcelain or applying a polymer material or fiber reinforced composite material such as Sculpture/FibreKor® material, both available from Jeneric/Pentron Inc. onto the metal coping. After the covering material has been removed from the metal coping, the metal coping may be opaqued. The latter, along with the die may be invested using conventional investing techniques. The lost wax process is used to create the desired shape for the exterior of the dental restoration. The die with the coping and wax thereon is then invested in an investment material and the wax is then burned out leaving space for the ceramic to occupy. A ceramic or composite pellet or button is pressed into the investment space to provide the exterior to the dental restoration. FIG. 9 shows coping 90 disposed on die 92 in investment 93. A ceramic button 94 is positioned below plunger 96 and is to be pressed into space 98 created by the lost wax process. This allows for cementing into the mouth a ceramic-containing or composite containing restoration, which normally must be bonded into the mouth.

In still yet another embodiment herein, it may be desirable to provide the coping with a porcelain margin as opposed to a metal margin, for aesthetic purposes. In this instance, when the metal powder is applied to the die, it does not extend fully to the margins. The metal powder is applied to a point above the margin or shoulder region on the die. The process proceeds as above, with the covering layers and sintering step. After sintering, the covering layers are removed. The coping is positioned on the die and a porcelain layer such as an opaque porcelain such as Synspar® Opaque porcelain is applied to the metal coping, also not extending past the margin. Thereafter, a porcelain material, such as a margin porcelain, is applied onto the lower edge of the coping over the porcelain layer and extends to the margin on the die. The porcelain is preferably a margin porcelain such as Synspar® Margin Porcelain available from Jeneric/Pentron Inc. used in the manufacture of dental restorations, although any porcelain with an appropriate coefficient of thermal expansion which is compatible with the underlying die may be used herein to achieve the final result. By applying porcelain to the margin, the porcelain material is built upon a region lined with no metal and therefore, problems associated with the exposure of the metal at the edge of the coping are overcome. Moreover, the margin of the coping is strong and not prone to bending or breaking. The porcelains appear to act as a thermal barrier to help in holding the coping in place and to prevent margin creeping and lifting. It is then sintered and the porcelain steps may be repeated again to achieve optimum results. Thereafter, the coping is built with more porcelain to provide the finally desired exterior of the restoration.

Figure 10:
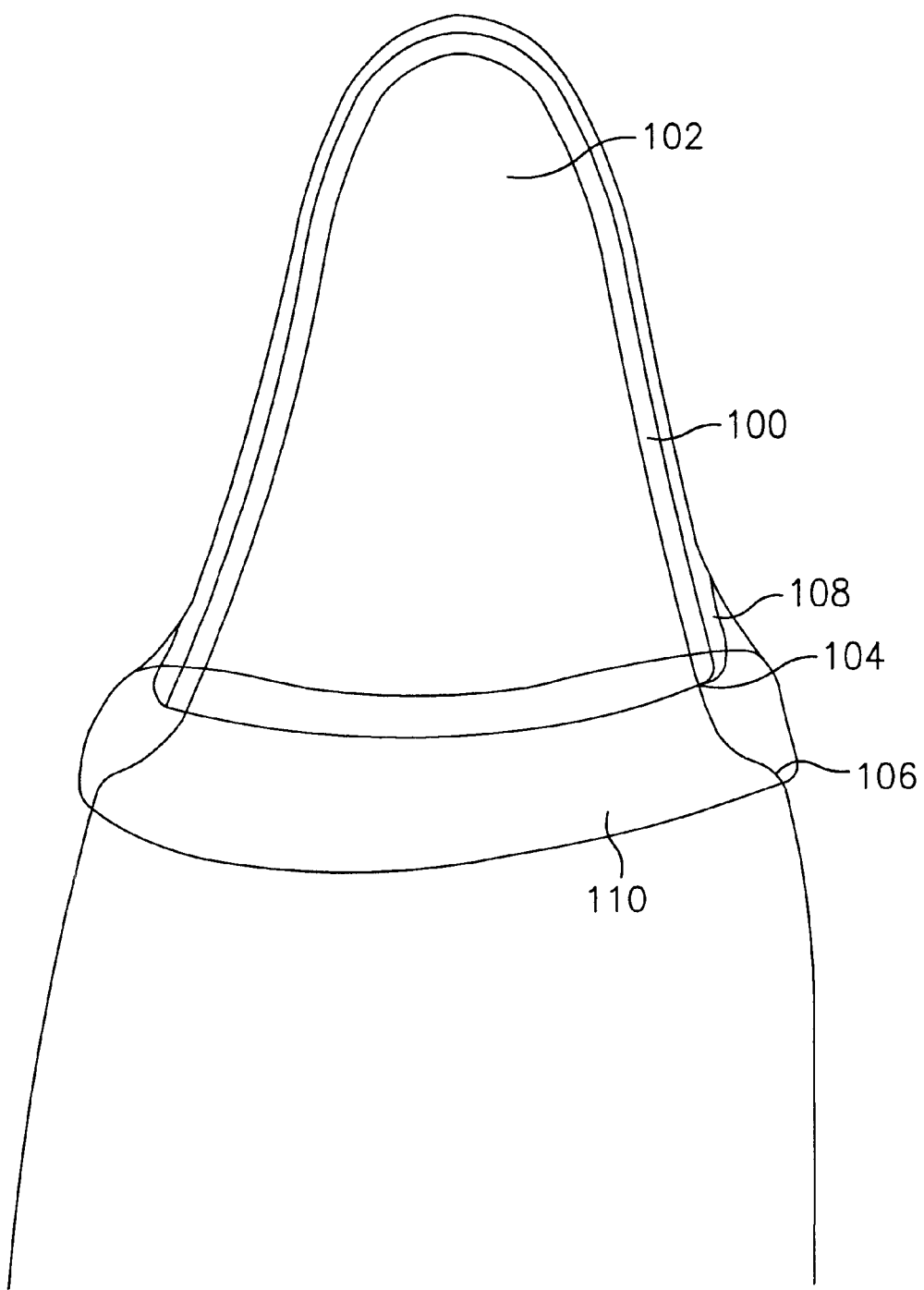
FIG. 10 is a cross-sectional view of a die with materials thereon in the manufacture of a dental restoration in accordance with a process herein.

FIG. 10 depicts a coping of the invention wherein a metal layer 100 is applied on die 102 to a point 104 above the margin 106. The metal layer is covered and sintered to obtain coping 100. A porcelain layer 108 such as an opaque porcelain is applied on metal coping 100, also to point 104. A margin porcelain material 110 is applied along margin 106 and overlaps the lower edge of metal coping 100 and porcelain layer 108.

In an alternate embodiment herein, a method of manufacturing dental restorations is provided obviating the need to duplicate the master die or model of the tooth to be restored. In the process herein, a dentist takes an impression of the tooth or teeth to be restored. A master die is then prepared from the impression using a suitable die material. From the master die, the actual restoration will be prepared.

Figure 11:
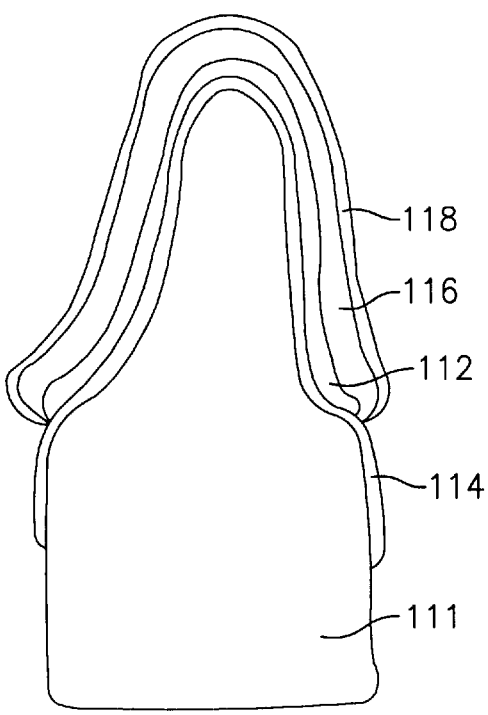
FIG. 11 is a cross-sectional view of a die with materials thereon in the manufacture of a dental restoration in accordance with a process herein.
Figure 12:
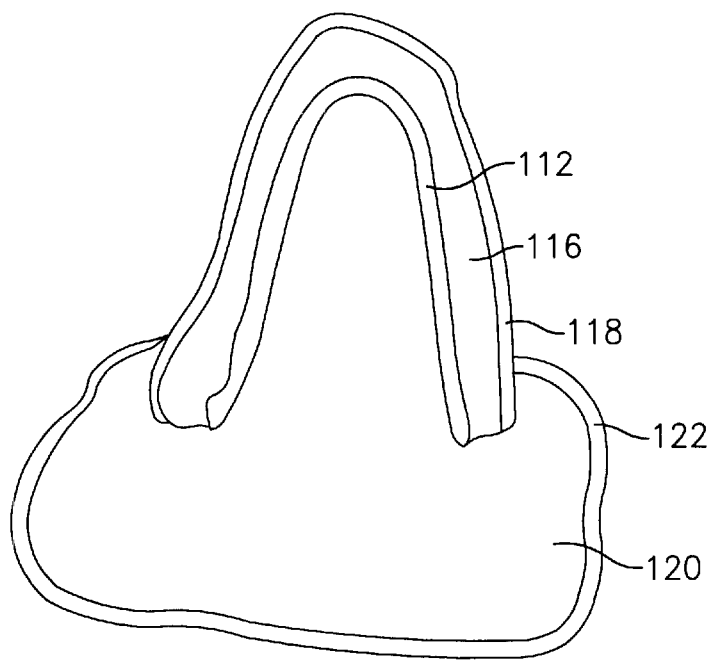
FIG. 12 is a cross-sectional view of the materials of FIG. 11 removed from the die and underfilled with material.

The die as shown in FIG. 11 with all the layers thereon is then dried. Die 111 is shown with metal powder layer 112 applied over die spacer layer 114. Covering layers 116 and 118 are applied thereafter. As noted in FIG. 11, the covering layers do not extend past the metal layer, so that all layers can be easily removed as a single unit as shown in FIG. 12. As the layers dry, they dry together to form a single unit of a metal coping, refractory die and refractory powder. Thereafter, the die having this dried unit of metal coping, refractory die and refractory powder is soaked in acetone for a period of time, about 8 to 10 minutes. This treat enables the unit of the metal coping, refractory die and refractory powder layer to be removed easily from the master die.

The underside of the coping unit is filled in with a refractory die material 120 which may be further coated with a refractory powder 122 as shown in FIG. 12. These materials are then left to dry, preferably for about ten minutes. The refractory die material is used to provide a base or platform for the coping unit so that the coping will maintain its shape during firing. Thereafter, the unit is fired to provide a high strength metal restoration. The sintering range depends upon the metal or alloy being used. The sintering temperature is close to but below the melting temperature of the metal/alloy. After sintering, the outer shell can be broken off easily with one's hand to expose the sintered coping. The coping is then easily removed from the die absent any adherence problems.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains.

Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for making a dental restoration comprising:
   forming a model of one or more teeth;
   coating the model with metal or alloy powder;
   applying a covering material onto the model coated with metal or alloy powder wherein the covering material is applied at a thickness equal to or less than about 8 mm;
   sintering the model coated with metal or alloy powder and covering material in a furnace to form a coping; and
   removing the covering material from the coping.

2. The method of claim 1 wherein the covering material comprises a refractory die material.

3. The method of claim 1 wherein the metal powder comprises a mixture of coarse and fine particles.

4. The method of claim 1 wherein the covering material comprises a refractory powder and a liquid vehicle.

5. The method of claim 4 wherein the liquid vehicle is selected from alcohol and acetone.

6. The method of claim 1 further comprising coating the covering material with a high temperature refractory material.

7. The method of claim 6 wherein the high temperature refractory material is selected from a refractory oxide.

8. The method of claim 7 wherein the refractory oxide is selected from alumina and silica.

9. The method of claim 1 wherein the coarse particles comprise particles in the range of from about 5 to about 50 microns.

10. The method of claim 1 wherein the fine particles comprise particles less than about 5 microns in size.

11. The method of claim 1 wherein the metal or alloy powder comprises a non-oxidizing metal.

12. The method of claim 11 wherein the non-oxidizing metal is selected from one or more precious metals, non-precious metals and alloys thereof.

13. The method of claim 3 wherein the metal or alloy powder is selected from one or more of gold, platinum, silver and alloys thereof.

14. The method of claim 1 wherein a binder is mixed with the metal or alloy powder prior to coating the model.

15. The method of claim 14 wherein the metal or alloy powder is present in an amount of about 90 to about 99 percent by weight and the binder is present in an amount of about 1 to about 10 percent by weight.

16. The method of claim 14 wherein the binder is selected from wax, ammonium caseinate, ammonium stearate, pectin, hexamine, ethyl cellulose, anthracene, triacetyl starch, dulcin, carbazole and tetraphenyl ethylene.

17. The method of claim 1 wherein the coarse particles comprise an average particle size of about 25 microns and wherein the fine particles are less than about 5 microns.

18. The method of claim 1 further comprising applying a die spacer material to the model prior to application of the metal or alloy powder.

19. The method of claim 1 wherein applying the covering material onto the model coated with metal or alloy powder comprises painting the covering material onto the metal powder with a brush.

20. The method of claim 6 whereincoating the covering material with a high temperature refractory material comprises dusting the high temperature refractory material onto the covering material.

21. The method of claim 1 wherein the coarse particles comprise atomized particles and the fine particles comprise precipitated particles.

22. A method for making a dental restoration comprising:
forming a model of one or more teeth;
coating the model with metal or alloy powder;
covering the model coated with metal powder with a covering material;
covering the covering material with a high temperature refractory material;
sintering the model coated with metal powder and covering material in a furnace to form a coping; and
removing the covering material with the high temperature refractory material from the coping.

23. A dental restoration formed by the process of claim 1.

24. A dental restoration formed by the process of claim 22.

25. A method for making a dental restoration comprising:
forming a model of one or more teeth;
coating the model with metal or alloy powder;
covering the model coated with metal powder with a covering material;
allowing the metal powder and covering material to dry to form a unit;
removing the dried metal powder and covering material unit from the model;
filling the understructure of the unit with covering material;
sintering the unit in a furnace to form a coping; and
removing the covering material from the coping.

26. The method of claim 25 wherein the covering material comprises a refractory die material.

27. The method of claim 26 wherein the refractory die material is applied at a thickness equal to or less than 8 mm.

28. The method of claim 25 wherein the covering material comprises a refractory powder and a liquid vehicle.

29. The method of claim 28 wherein the liquid vehicle is selected from alcohol and acetone.

30. The method of claim 25 further comprising coating the covering material with a high temperature refractory material.

31. The method of claim 30 wherein the high temperature refractory material is selected from a refractory oxide.

32. The method of claim 31 wherein the refractory oxide comprises alumina or silica.

33. The method of claim 25 wherein the metal or alloy particles comprise a mixture of coarse and fine particles.

34. The method of claim 33 wherein the coarse particles comprise particles in the range of from about 5 to about 50 microns.

35. The method of claim 33 wherein the fine particles comprise particles less than about 5 microns in size.

36. The method of claim 25 wherein the metal or alloy powder comprises a non-oxidizing metal.

37. The method of claim 36 wherein the non-oxidizing metal is selected from one or more precious metals, non-precious metals and alloys thereof.

38. The method of claim 25 wherein the metal or alloy powder is selected from one or more of gold, platinum, silver and alloys thereof.

39. The method of claim 25 wherein a binder is mixed with the metal or alloy powder prior to coating the model.

40. The method of claim 39 wherein the metal or alloy powder is present in an amount of about 90 to about 99 percent by weight and the binder is present in an amount of about 1 to about 10 percent by weight.

41. The method of claim 39 wherein the binder is selected from wax, ammonium caseinate, ammonium stearate, pectin, hexamine, ethyl cellulose, anthracene, triacetyl starch, dulcin, carbazole and tetraphenyl ethylene.

42. The method of claim 33 wherein the coarse particles comprise an average particle size of about 25 microns.

43. The method of claim 25 wherein a die spacer material is applied to the model prior to application of the metal powder.

44. A dental restoration formed by the process of claim 25.

45. The method of claim 25 wherein the model is a master die.

46. A method for making a dental restoration comprising:
forming a model of a dental part to be produced;
coating the model with metal or alloy powder;
applying a covering material onto the model coated with metal or alloy powder wherein the covering material is applied at a thickness equal to or less than about 8 mm;
sintering the model coated with metal or alloy powder and covering material in a furnace to form a dental part; and
removing the covering material from the dental part.

47. A dental restoration formed by the process of claim 46.

48. A method for making a dental restoration comprising:
forming a model of one or more teeth;
coating the model with metal or alloy powder;
applying a first porcelain material on the metal or alloy powder;
sintering the model coated with metal or alloy powder and porcelain in a furnace to form a coping having a first porcelain thereon; and
applying a second porcelain material on the first porcelain material and sintering the coping.

49. The method of claim 48 wherein the metal or alloy powder comprises a non-oxidizing metal.

50. The method of claim 49 wherein the non-oxidizing metal is selected from one or more precious metals, non-precious metals and alloys thereof.

51. The method of claim 48 wherein the metal or alloy powder is selected from one or more of gold, platinum, silver and alloys thereof.

52. The method of claim 48 wherein a binder is mixed with the metal or alloy powder prior to coating the model.

53. The method of claim 52 wherein the metal or alloy powder is present in an amount of about 90 to about 99 percent by weight and the binder is present in an amount of about 1 to about 10 percent by weight.

54. The method of claim 52 wherein the binder is selected from wax, ammonium caseinate, ammonium stearate, pectin, hexamine, ethyl cellulose, anthracene, triacetyl starch, dulcin, carbazole and tetraphenyl ethylene.

55. The method of claim 47 wherein a die spacer material is applied to the model prior to application of the metal or alloy powder.

56. The method of claim 48 wherein the first porcelain material is applied at a thickness in the range of about 0.1 to about 1.5.

57. A dental restoration formed by the process of claim 48.

58. A method for making a dental restoration comprising:
forming a model of one or more teeth;
coating the model with powder of a first metal or alloy;
placing a reservoir of a second metal or alloy onto the model coated with the powder of the first metal or alloy, wherein the second metal or alloy has a fusing temperature lower than the fusing temperature of the first metal or alloy;
covering the model coated with the powder of first metal or alloy and the reservoir of the second metal or alloy with covering material; and sintering the model to form a coping.

59. The method of claim 58 wherein the reservoir comprises a solid piece of metal or alloy.

60. The method of claim 58 wherein the reservoir comprises a metal or an alloy powder held together by a binder.

61. The method of claim 58 wherein the reservoir is in the shape of a sphere, bar, oval, or block.

62. The method of claim 58 wherein the reservoir comprises pure gold.

63. The method of claim 58 wherein the reservoir comprises a gold alloy.

64. The method of claim 58 wherein the reservoir is placed proximate the top of the model.

65. The method of claim 58 wherein the powder of the first metal or alloy is in the form of a sheet.

66. The method of claim 63 wherein the gold alloy comprises gold in combination with an oxidizing element.

67. The method of claim 58 wherein a die spacer material is applied to the model prior to application of the powder of the first metal or alloy.

68. The method of claim 58 wherein a die spacer material is applied onto the powder of the first metal or alloy and reservoir after placement of the reservoir of the second metal or alloy onto the model.

69. The method of claim 58 wherein the covering material comprises a refractory die material.

70. The method of claim 69 wherein the refractory die material is applied at a thickness equal to or less than 8 mm.

71. The method of claim 58 wherein the covering material comprises a refractory powder.

72. The method of claim 58 further comprising coating the covering material with a high temperature refractory material.

73. The method of claim 72 wherein the high temperature refractory material is selected from a refractory oxide.

74. The method of claim 73 wherein the refractory oxide comprises alumina or silica.

75. The method of claim 58 wherein the powder of a first metal or alloy comprises a mixture of coarse particles and fine particles.

76. The method of claim 75 wherein the coarse particles are equal to or below −270 mesh.

77. The method of claim 76 wherein the fine particles comprise particles less than about 5 microns in size.

78. The method of claim 58 wherein the first metal or alloy comprises a non-oxidizing metal.

79. The method of claim 58 wherein the first metal or alloy is selected from one or more precious metals, non-precious metals and alloys thereof.

80. The method of claim 58 wherein the first metal or alloy comprises gold, platinum, silver or alloys thereof.

81. The method of claim 58 wherein a binder is mixed with the powder of the first metal or alloy prior to coating the model.

82. The method of claim 81 wherein the powder of the first metal or alloy and binder are in the form of a sheet.

83. The method of claim 82 wherein the powder of the first metal or alloy is present in an amount of about 90 to about 99 percent by weight and the binder is present in an amount of about 1 to about 10 percent by weight.

84. The method of claim 83 wherein the binder is selected from wax, ammonium caseinate, ammonium stearate, pectin, hexamine, ethyl cellulose, anthracene, triacetyl starch, dulcin, carbazole, tetraphenyl ethylene and mixtures thereof.

85. The method of claim 58 wherein the powder of the first metal or alloy comprises atomized powder and precipitated powder.

86. A dental restoration formed by the process of claim 58.

87. A method for making a dental restoration comprising:
forming a model of one or more teeth, wherein the model comprises a margin area;
coating the model with powder of a metal or alloy to a point above the margin area;
covering the model coated with powder with a covering material;
sintering the model coated with powder in a furnace to form a metal coping;
removing the covering material from the metal coping;
applying a first porcelain material on the metal coping;
applying a second porcelain material on the model along the margin area; and
firing the coping and die coated with first and second porcelain material in a furnace.

88. The method of claim 87 wherein the powder comprises a non-oxidizing metal.

89. The method of claim 88 wherein the non-oxidizing metal is selected from one or more precious metals, non-precious metals and alloys thereof.

90. The method of claim 87 wherein the metal or alloy powder is selected from one or more of gold, platinum, silver and alloys thereof.

91. The method of claim 87 wherein a binder is mixed with the metal or alloy powder prior to coating the model.

92. The method of claim 91 wherein the metal or alloy powder is present in an amount of about 90 to about 99 percent by weight and the binder is present in an amount of about 1 to about 10 percent by weight.

93. The method of claim 91 wherein the binder is selected from wax, ammonium caseinate, ammonium stearate, pectin, hexamine, ethyl cellulose, anthracene, triacetyl starch, dulcin, carbazole and tetraphenyl ethylene.

94. The method of claim 87 wherein a die spacer material is applied to the model prior to application of the metal or alloy powder.

95. The method of claim 87 wherein the metal or alloy powder comprises atomized powder and precipitated powder.

96. A dental restoration formed by the process of claim 87.

97. The method of claim 87 wherein the powder of the metal or alloy is in the form of a sheet.

98. The method of claim 87 wherein the covering material comprises a refractory die material.

99. The method of claim 87 wherein the refractory die material is applied at a thickness equal to or less than 8 mm.

100. The method of claim 87 wherein the covering material comprises a refractory powder and a liquid vehicle.

101. The method of claim 100 wherein the liquid vehicle is selected from alcohol and acetone.

102. The method of claim 87 further comprising coating the covering material with a high temperature refractory material.

103. The method of claim 102 wherein the high temperature refractory material is selected from a refractory oxide.

104. The method of claim 103 wherein the refractory oxide comprises alumina.

105. The method of claim 1 wherein the model is dried prior to sintering.

106. The method of claim 1 further comprising applying a porcelain or composite material to the coping.

107. The method of claim 106 wherein the porcelain or composite is pressed onto the coping.

108. The method of claim 106 wherein a bonder coat is applied to the coping prior to application of the porcelain or composite material.

109. The method of claim 108 wherein the bonder coat comprises a metal or alloy.

110. The method of claim 109 wherein the metal or alloy from the bonder coat comprises gold, copper, indium, tin, rhodium, palladium, gallium, platinum, iridium or mixtures thereof.

111. The method of claim 1 wherein sintering is carried out in a reducing atmosphere.

112. The method of claim 1 further comprising placing a graphite cover over the covering material prior to sintering.

113. The method of claim 2 wherein the covering material further comprises a carbonaceous material.

114. The method of claim 22 wherein the high temperature refractory material comprises a refractory oxide.

115. The method of claim 14 wherein the refractory oxide comprises alumina or silica.

116. The method of claim 25 further comprising applying a porcelain or composite material to the coping.

117. The method of claim 116 wherein the porcelain or composite is pressed onto the coping.

118. The method of claim 116 wherein a bonder coat is applied to the coping prior to application of the porcelain or composite material.

119. The method of claim 118 wherein the bonder coat comprises a metal or alloy.

120. The method of claim 119 wherein the metal or alloy from the bonder coat comprises gold, copper, indium, tin, rhodium, palladium, gallium, platinum, iridium or mixtures thereof.

121. The method of claim 25 wherein sintering is carried out in a reducing atmosphere.

122. The method of claim 25 further comprising placing a graphite cover over the covering material prior to sintering.

123. The method of claim 26 wherein the covering material further comprises a carbonaceous material.

124. The method of claim 48 wherein the first porcelain comprises an opaque porcelain.

125. The method of claim 58 wherein the reservoir is bonded, melted or mechanically adhered to the powder of the first metal or alloy.

126. The method of claim 58 wherein the reservoir has a mass equal to about the weight of the powder of a first metal or alloy.

127. The method of claim 58 further comprising removing the covering material from the coping.

128. The method of claim 127 further comprising applying a porcelain or composite material to the coping.

129. The method of claim 128 wherein the porcelain or composite is pressed onto the coping.

130. The method of claim 128 wherein a bonder coat is applied to the coping prior to application of the porcelain or composite material.

131. The method of claim 130 wherein the bonder coat comprises a metal or alloy.

132. The method of claim 131 wherein the metal or alloy from the bonder coat comprises gold, copper, indium, tin, rhodium, palladium, gallium, platinum, iridium or mixtures thereof.

133. The method of claim 58 wherein sintering is carried out in a reducing atmosphere.

134. The method of claim 58 further comprising placing a graphite cover over the covering material prior to sintering.

135. The method of claim 69 wherein the covering material further comprises a carbonaceous material.

136. A method for making a dental restoration comprising:

forming a model of one or more teeth;

placing a bar or pontic on the model;

coating the model and bar or pontic with metal or alloy powder;

applying a covering material onto the model coated with metal or alloy powder;

sintering the model coated with metal or alloy powder and covering material in a furnace to form a coping; and removing the covering material from the coping.

137. The method of claim 136 wherein the bar or pontic is manufactured by extrusion, casting, shaping metal powder into a shape, or shaping sheets of metal powder into a shape.

138. The method of claim 136 wherein the covering material comprises a refractory die material.

139. The method of claim 136 wherein the metal powder comprises a mixture of coarse and fine particles.

140. The method of claim 136 wherein the covering material comprises a refractory powder and a liquid vehicle.

141. The method of claim 136 wherein the liquid vehicle is selected from alcohol and acetone.

142. The method of claim 136 further comprising coating the covering material with a high temperature refractory material.

143. The method of claim 142 wherein the high temperature refractory material is selected from a refractory oxide.

144. The method of claim 143 wherein the refractory oxide is selected from alumina and silica.

145. The method of claim 139 wherein the coarse particles comprise particles in the range of from about 5 to about 50 microns.

146. The method of claim 139 wherein the fine particles comprise particles less than about 5 microns in size.

147. The method of claim 136 wherein the metal or alloy powder comprises a non-oxidizing metal.

148. The method of claim 147 wherein the non-oxidizing metal is selected from one or more precious metals, non-precious metals and alloys thereof.

149. The method of claim 136 wherein the metal or alloy powder is selected from one or more of gold, platinum, silver and alloys thereof.

150. The method of claim 136 wherein a binder is mixed with the metal or alloy powder prior to coating the model.

151. The method of claim 150 wherein the metal or alloy powder is present in an amount of about 90 to about 99 percent by weight and the binder is present in an amount of about 1 to about 10 percent by weight.

152. The method of claim 150 wherein the binder is selected from wax, ammonium caseinate, ammonium stearate, pectin, hexamine, ethyl cellulose, anthracene, triacetyl starch, dulcin, carbazole and tetraphenyl ethylene.

153. The method of claim 139 wherein the coarse particles comprise an average particle size of about 25 microns and wherein the fine particles are less than about 5 microns.

154. The method of claim 136 further comprising applying a die spacer material to the model prior to application of the metal or alloy powder.

155. The method of claim 136 wherein the step of applying the covering material onto the model coated with metal or alloy powder comprises painting the covering material onto the metal powder with a brush.

156. The method of claim 142 wherein the step of coating the covering material with a high temperature refractory material comprises dusting the high temperature refractory material onto the covering material.

157. The method of claim 139 wherein the coarse particles comprise atomized particles and the fine particles comprise precipitated particles.

158. A dental restoration formed by the process of claim 136.

* * * * *